United States Patent
Tsuji et al.

[11] Patent Number: 6,090,089
[45] Date of Patent: Jul. 18, 2000

[54] TOPSHEET FOR DISPOSABLE BODY FLUIDS ABSORBENT GARMENT AND METHOD OF MAKING SAME

[75] Inventors: Tomoko Tsuji; Hiroki Goda, both of Kagawa-ken; Hisashi Takai, Ehime-ken, all of Japan

[73] Assignee: Uni-Charm Corporation, Ehime-ken, Japan

[21] Appl. No.: 09/014,614

[22] Filed: Jan. 28, 1998

[30] Foreign Application Priority Data

Jan. 31, 1997 [JP] Japan .................................. 9-018958

[51] Int. Cl.[7] ............................. A61F 13/15; B31F 53/00
[52] U.S. Cl. ........................ 604/385.1; 604/383; 156/219
[58] Field of Search ............................... 604/383, 385.1, 604/378; 156/219

[56] References Cited

U.S. PATENT DOCUMENTS

| 4,323,068 | 4/1982 | Aziz ........................................ 604/370 |
| 4,324,246 | 4/1982 | Mullane et al. . |
| 5,368,910 | 11/1994 | Langdon . |
| 5,514,105 | 5/1996 | Goodman, Jr. et al. ................. 604/370 |

FOREIGN PATENT DOCUMENTS

| 57-17081 | 4/1982 | Japan . |
| 4-82977 | 3/1992 | Japan . |

*Primary Examiner*—John G. Weiss
*Assistant Examiner*—Catherine Cogut
*Attorney, Agent, or Firm*—Lowe Hauptman Gopstein Gilman & Berner

[57] ABSTRACT

A liquid-permeable topsheet used in a disposable body fluids absorbent garment has planar portions substantially extending in a horizontal plane, a plurality of ribs rising from the planar portions and extending parallel one to another, each presenting a cross-section in an inverted v-shape, and liquid-passages extending downward from the planar portions and thereby eliminate any appreciation that eruption and/or stuffiness might be caused by contact of the topsheet with the skin of a wearer.

7 Claims, 4 Drawing Sheets

TOPSHEET FOR DISPOSABLE BODY FLUIDS ABSORBENT GARMENT AND METHOD OF MAKING SAME

BACKGROUND OF THE INVENTION

This invention relates generally to a topsheet used in a body fluid absorbent garment such as a disposable diaper, sanitary napkin or the like.

Japanese Patent Application Publication (Kokoku) No. Sho57-17081 discloses a topsheet comprising a plastic film formed with a plurality of tapered liquid-passages. A smooth upper surface of the film is intended to contact a wearer's skin. The liquid-passages open in the upper surface of the film and extend downward from the upper surface toward the lower surface of the film.

Japanese Laid-Open Patent Application (Kokai) No. Hei4-82977 discloses a topsheet comprising a first pair of ribs extending parallel to each other, another pair of ribs extending parallel to each other and orthogonally to the first pair, and air-permeable and moisture-permeable openings formed in regions defined by the two pairs of ribs.

The liquid-passages and the openings provided in the foregoing topsheet are certainly effective to transfer discharged body fluids to a liquid-absorbent core directly underlying the topsheet.

However, the topsheet disclosed in the Japanese Patent Application Publication No. Sho57-17081 has its upper surface except the openings of the respective liquid-passages in direct contact with the wearer's skin. The topsheet disclosed in the Japanese Laid-Open Patent Application No. Hei4-82977 has the ribs each presenting a cross-sectional shape curved so as to widen toward an absorbent core immediately underlying the ribs. Such a topsheet contacts the wearer's skin not only crests of the respective ribs but also portions adjacent the crests.

With these known topsheets, an area over which the topsheet contacts the wearer's skin increases as an area occupied by the openings in the upper surface (opening area ratio) decreases. A garment using such topsheet often causes stuffiness and/or eruption due to wearing the garment.

SUMMARY OF THE INVENTION

In view of the problems described above, it is a principal object of the invention to provide an improved body fluids absorbent garment that allows a wearer to be free from skin eruption and/or stuffiness even when the topsheet used in the garment has a relatively low opening area ratio.

The object set forth above is achieved, according to one aspect of the invention, with a disposable body fluid absorbent garment that comprises a topsheet which is liquid-permeable, a liquid-impermeable backsheet and a liquid-absorbent core disposed therebetween. The topsheet has an upper surface intended to contact with the skin of a wearer and a lower surface opposed to the upper surface. The upper surface has planar portions extending substantially in a horizontal plane, and a plurality of ribs extending parallel to one another in one direction. Each rib rises from the lower surface toward the upper surface in each of the planar portions and presents an inverted V-shape in cross-section. Liquid-passages opening in the planar portions extend downward through the lower surface from the upper surface and are arranged intermittently with respect to the direction in which the ribs extend.

The object set forth above is achieved, according to another aspect of the invention, by a method for making a liquid-permeable topsheet for a disposable body fluids absorbent garment. The method comprises the step of feeding a web of at least one of nonwoven fabric and thermoplastic synthetic resin film between at least one pair of first and second rolls arranged parallel so as to engage each other and emboss the web.

The first roll is formed on a smooth surface thereof with a plurality of ribs extending in parallel to an axis of the first roll. Each rib has an inverted V-shape cross-section and pyramidal recesses are arranged between each pair of the adjacent ribs intermittently in parallel to the axis. The second roll is formed on a smooth surface thereof with first pyramids adapted to be received by the pyramidal recesses and second pyramids arranged on the same circumferential line on the second roll alternately with the first pyramids with the respectively adjacent ribs therebetween.

The web is fed between the first and second rolls to form liquid-passages extending in the direction of the web thickness toward one direction at least under the cooperation of the pyramidal recesses with the pyramids, on the one hand, and ribs each presenting a cross-section in an inverted V-shape and projecting toward the other direction are formed at least under the cooperation of the ribs with the first and second pyramids, on the other hand.

DESCRIPTION OF THE PREFERRED EMBODIMENT

Figure 1:
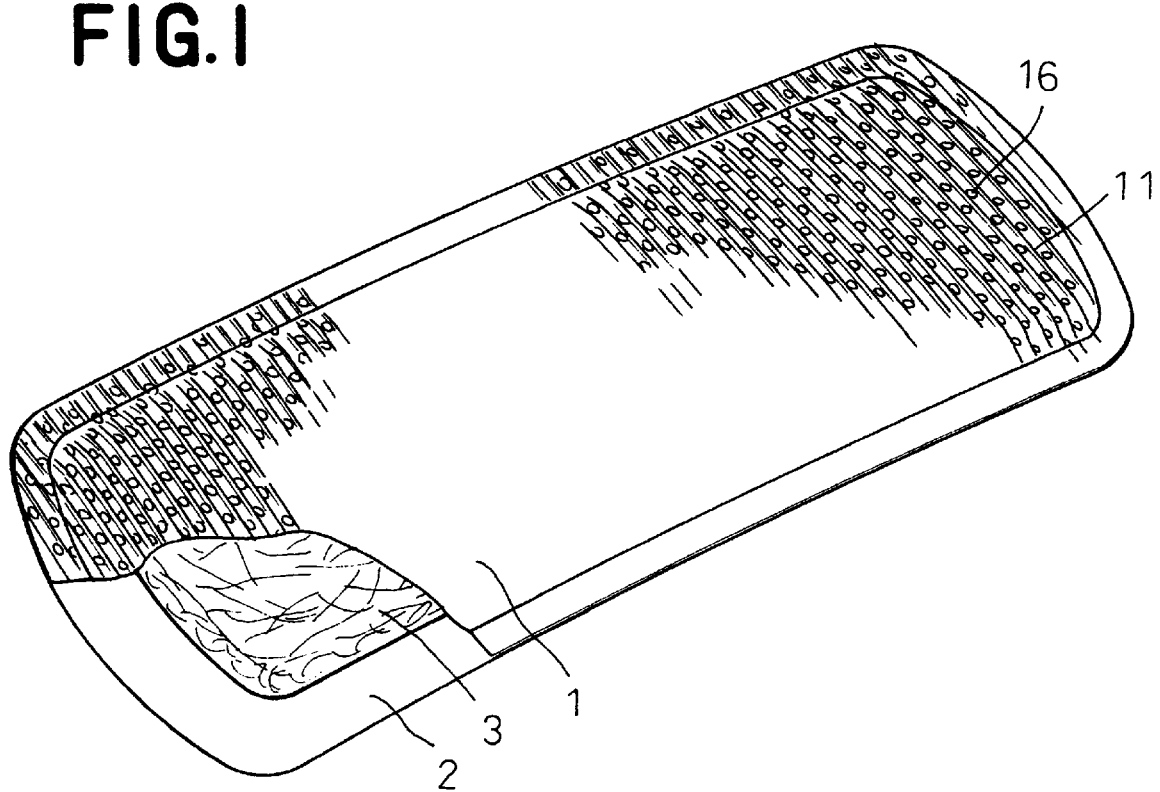
FIG. 1 is a perspective view of a sanitary napkin as partially broken away.

A sanitary napkin shown by FIG. 1 in a fragmentary perspective view as partially broken away comprises a liquid-permeable topsheet 1 defining a surface intended to be in contact with the skin of a wearer, a liquid-impermeable backsheet 2 defining a surface out of contact with the skin of a wearer and a liquid-absorbent core 3 disposed between sheets 1, 2. The topsheet 1 and the backsheet 2 are identical to each other in shape as well as in size and placed one upon another. Over their portions extending outward beyond a peripheral edge of the absorbent core 3, sheets 1, 2 are bonded together with heat-sealing or adhesive agent (not shown).

The topsheet 1 is made of a nonwoven fabric, more preferably of a nonwoven fabric containing thermoplastic synthetic fibers of 60~100% by weight or a thermoplastic synthetic resin film and has a plurality of ribs 11 extending parallel one to another transversely of the napkin and a plurality of liquid-passages 16 formed between each pair of adjacent ribs.

The backsheet 2 is made of a thermoplastic synthetic resin film and the absorbent core 3 is formed from fluff pulp or a mixture of fluff pulp and a hydrocolloid material of high water absorptivity.

Figure 2:
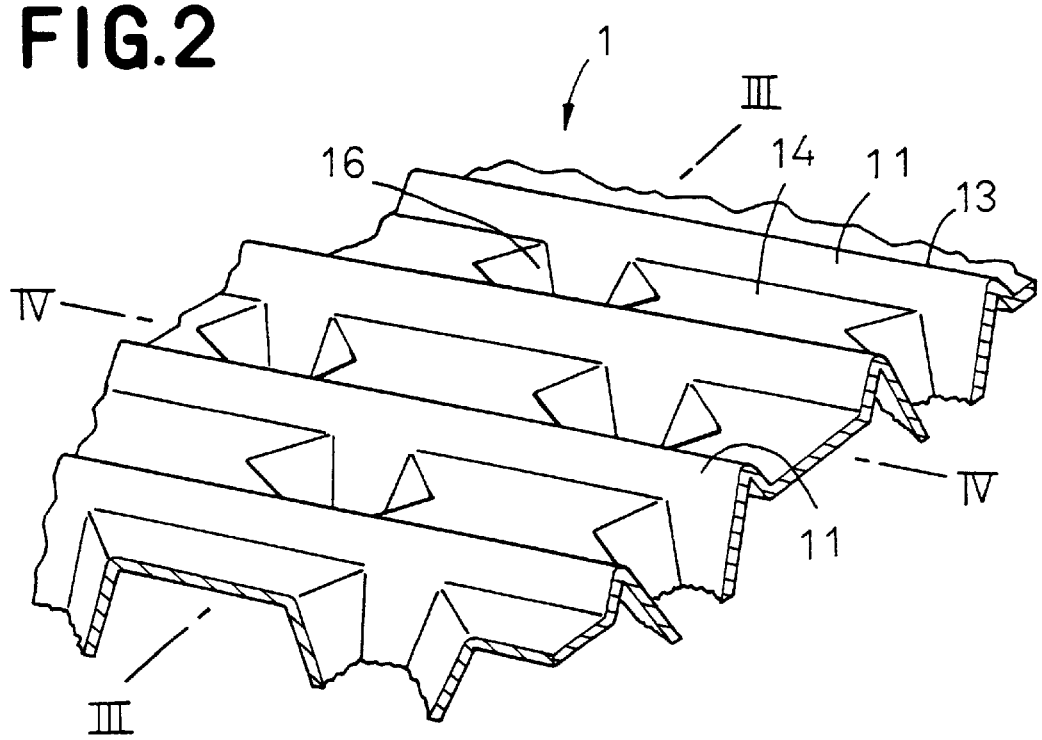
FIG. 2 is a fragmentary perspective view of a topsheet according to the invention in an enlarged scale.
Figure 3:
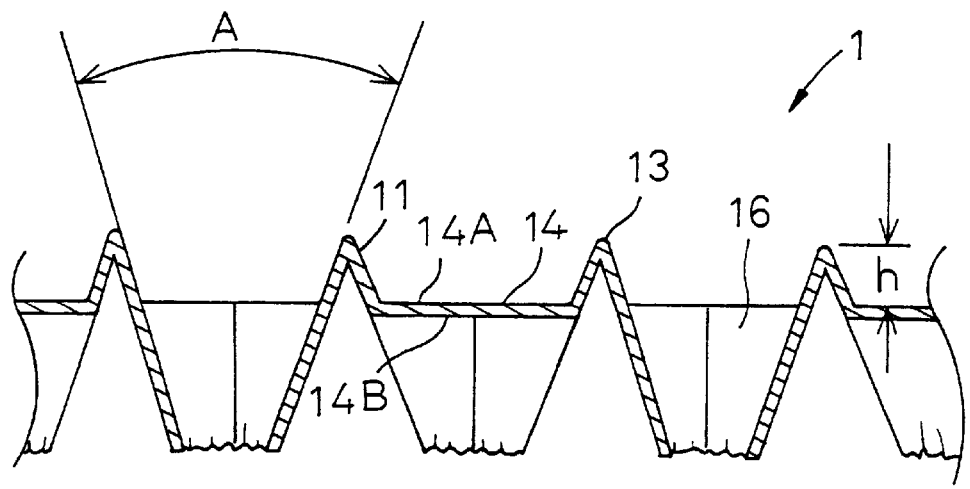
FIG. 3 is a sectional view taken along line III—III in FIG. 2.
Figure 4:
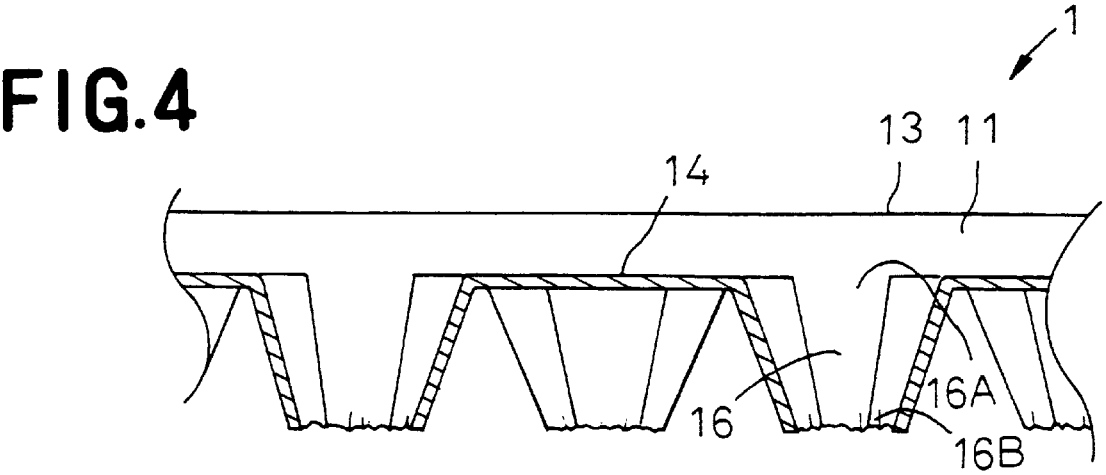
FIG. 4 is a sectional view taken along line IV—IV in FIG. 2.

FIGS. 2, 3 and 4 are fragmentary perspective views showing the topsheet 1 in an enlarged scale and sectional views taken along lines III—III, IV—IV, respectively, in FIG. 2. Each of ribs 11 on the topsheet 1 presents a generally inverted V-shaped cross-section and has a crest 13 defined by an included angle of 10~90°. The crests 13 of the adjacent ribs 11 are spaced apart from each other by 0.5~5 mm. Between each pair of the adjacent ribs 11, the topsheet 1 is formed with both planar portions 14 (extending in a substantially horizontal plane) and liquid-passages 16.

Each of the planar portions 14 has an upper surface 14A facing the skin of a wearer and a lower surface 14B remote from the skin of the wearer. Each of the ribs 11 rises from the upper surface 14A so that the crest 13 lies at a height of h above the upper surface 14A. The height h is preferably in a range of 0.2~2 mm.

Each of the liquid-passages 16 extends downward from an upper opening 16A in the upper surface 14A beyond the lower surface 14B to a lower opening 16B. A length of the liquid-passage 16 as measured from the upper opening 16A to the lower opening 16B is preferably dimensioned to be in a range of 0.2~3 mm. A diameter of the liquid-passage 16 is gradually reduced from the upper opening 16A toward the lower opening 16B preferably so that transversely opposite walls as viewed in FIG. 3 defining this liquid-passage 16 include an angle A of 20~110° therebetween and the lower opening 16B has an area of 0.1~2 mm$^2$. While the cross-sectional shape of the liquid-passage 16 as viewed in the radial direction is not critical, it is preferable in general that the liquid-passage 16 has a circular or polygonal cross-section not only from the viewpoint of appearance but also from the viewpoint of manufacturing convenience. FIGS. 2 and 3 illustrate the upper opening 16A as presenting an equilateral hexagonal cross-section. Referring to FIG. 3, the walls defining each of the liquid-passages 16 slope down at the same angle as the angle at which the walls of the ribs 11 slope down so as to define continuous surfaces. The liquid-passages 16 are arranged at a pitch of 0.5~5 mm along the direction in which the ribs 11 extend.

The topsheet 1 described above is used with the lower openings 16B of the respective liquid-passages 16 in contact with the absorbent core 3 so that body fluids discharged onto the topsheet 1 may be transferred under a capillary action of the liquid-passages 16. To promote such transfer of body fluids, it will be effective to coat the topsheet 1 in the proximity of the lower openings 16B with an agent making the topsheet 1 hydrophilic if the topsheet 1 is made of a nonwoven fabric composed of hydrophobic thermoplastic synthetic fibers or a thermoplastic synthetic resin film. With the topsheet 1 adapted to be used in a manner as shown by FIG. 1 with the transversely extending ribs 11, the napkin is readily curved longitudinally of the body of a wearer as the napkin is held against the vaginal opening of the wearer. In addition, the presence of the ribs 11 serves to pre vent longitudinal creases from forming on the topsheet 1. Consequently, the napkin evenly f its to the body of the wearer around her vaginal opening and does not give her an uncomfortable feeling during wear. Furthermore, such topsheet is advantageous also in that, while the crests 13 of the respective ribs 11 are put in contact with the skin of the wearer as the napkin is worn, the planar portions 14 remain spaced from the skin of the wearer and thereby aeration channels (grooves) are formed between each pair of the adjacent ribs 11 extending transversely of the napkin. Such aeration channels serve to alleviate a possibility that the wearer might otherwise suffer from eruption and/or stuffiness.

Figure 5:
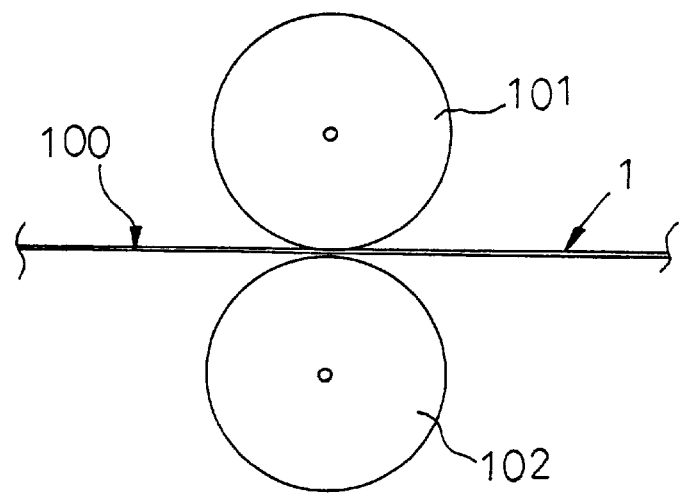
FIG. 5 is a side view of a pair of embossing rolls.
Figure 6:
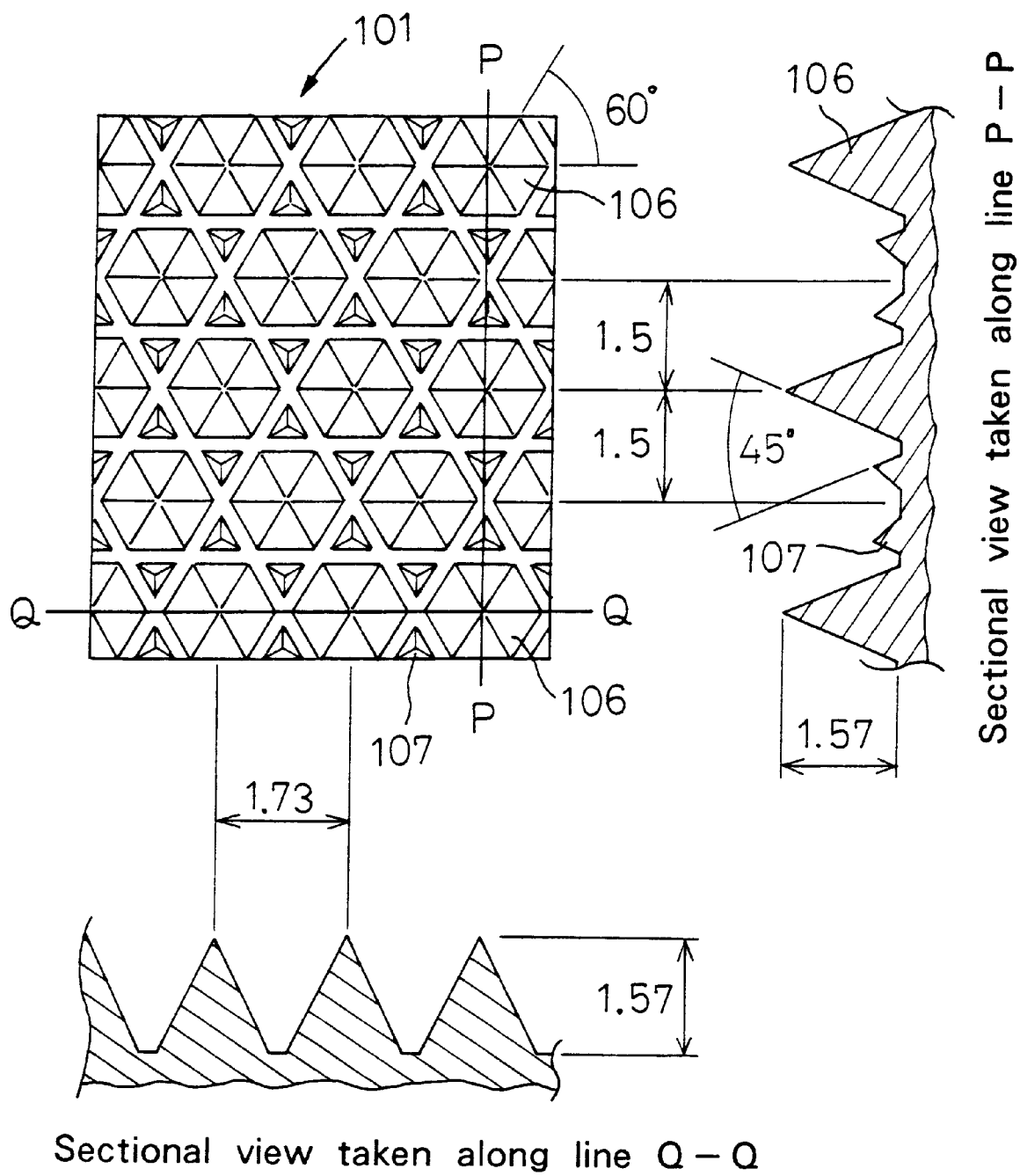
FIG. 6 is a fragmentary developed view of an upper roll.
Figure 7:
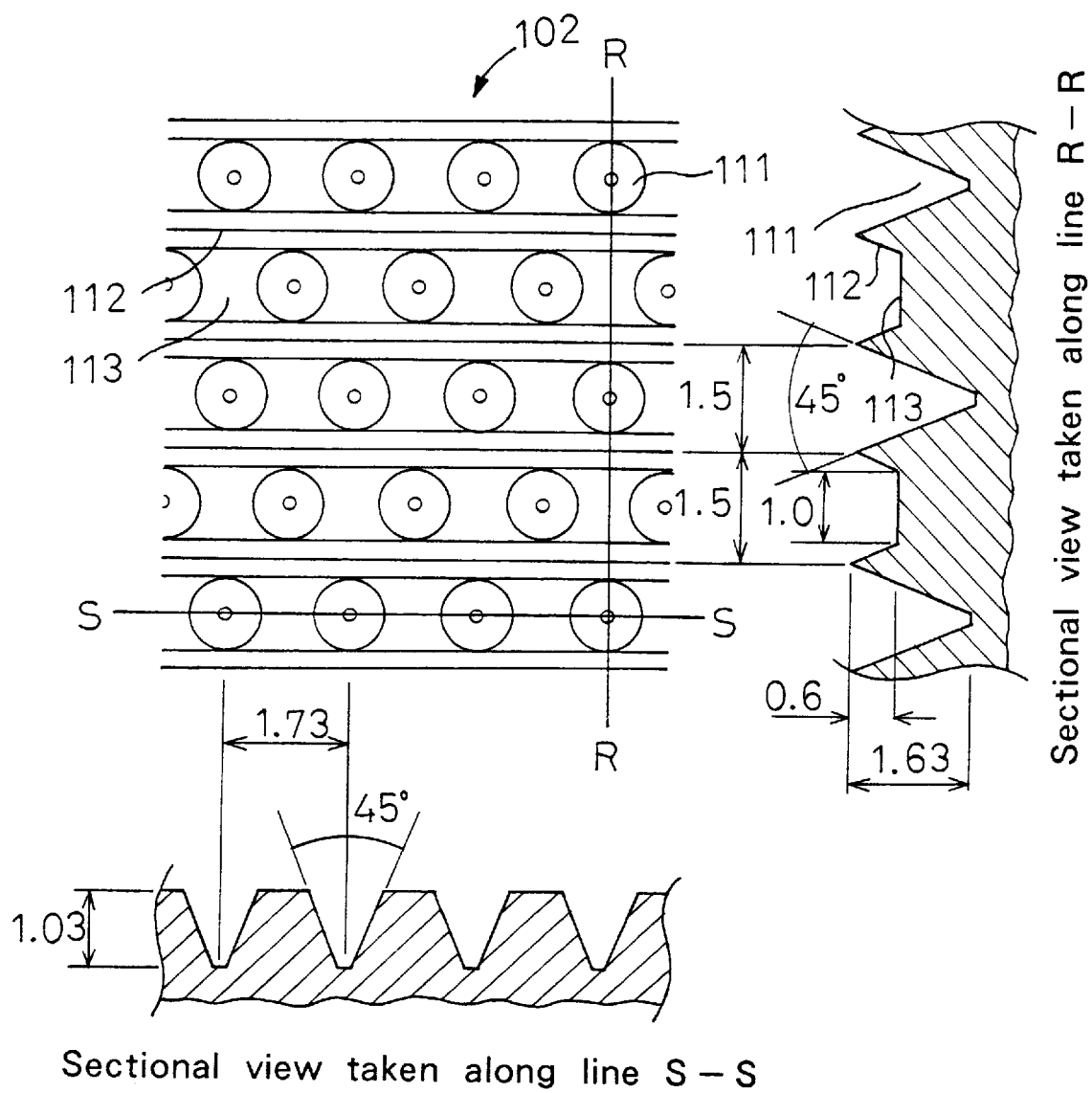
FIG. 7 is a fragmentary developed view of a lower roll.

FIGS. 5, 6 and 7 are a side view of a pair of embossing rolls 101, 102 used to treat a nonwoven fabric or film 100 and thereby to obtain the topsheet 1 (or its original roll), and respective fragmentary developed views of these rolls 101, 102. The axes of the respective rolls 101, 102 extend transversely as viewed in FIG. 6 and the respective rolls 101, 102 rotate vertically as viewed in FIG. 7. FIGS. 6, 7 include sectional views showing surface configurations of the respective rolls and dimension values in mm of important parts.

Referring to FIG. 6, the upper roll 101 is formed with hexagonal pyramids 106 each having a height of 1.57 mm at a pitch of 1.73 mm in the axial direction and at a pitch of 3.0 mm in the circumferential direction. Between a pair of the axially adjacent hexagonal pyramids 106, there is formed a relatively low trigonal pyramid 107. The crests of these trigonal pyramids are arranged on a line P—P defined by the hexagonal pyramids 106 aligned along the same circumferential line. Relative height of these hexagonal pyramids 106 and the trigonal pyramids 107 will be seen in a sectional view taken along the line P—P.

The lower roll 102 shown by FIG. 7 is formed with conical recesses 111 each having a depth of 1.63 mm at a pitch of 1.73 mm in the axial direction and at a pitch of 3.0 mm in the circumferential direction. In addition, the lower roll 102 is formed with a plurality of axially extending inverted V-shaped ribs 112 at a pitch of 1.5 mm in the circumferential direction. Between each pair of the axially adjacent recesses 111, there is formed a planar portion 113.

These upper and lower rolls 101, 102 are combined so that the hexagonal pyramids 106 on the upper roll 101 are received by the corresponding conical recesses 111 on the lower roll 102 and the ribs 112 lie between each pair of rows of the axially aligned hexagonal pyramids 106. At the same time, each of the ribs 112 lies between each pair of the circumferentially adjacent hexagonal pyramid 106 and trigonal pyramid 107 and squeezed between these two pyramids 106, 107. It should be understood that the upper and lower rolls 101, 102 are combined with each other so as to leave therebetween a predetermined clearance, for example, a clearance in the order of 0.04 mm. The pair of rolls 101, 102 adjusted as has been described above is supplied with a point-bonded nonwoven fabric 100 made of polypropylene/polyethylene composite fibers having a basis weight of 10~40 g/m$^2$, a fineness of 4 d and a length of 51 mm. The liquid-passages 16 and the ribs 11 are formed by the hexagonal pyramids 106 and the ribs 112, respectively, as the point-bonded nonwoven fabric 100 passes through the pair of rolls 101, 102. As a result, the topsheet 1 (or its original roll) is obtained, in which the lower openings 16B of the liquid-passages 16 have their areas of 0.2~0.3 mm$^2$, respectively, and their total area occupies 10~15% of a-surface area of the topsheet. The upper and lower rolls 101, 102 are adapted to squeeze the nonwoven fabric 100 at a predetermined pressure and also to heat the nonwoven fabric 100 at a predetermined temperature.

The novel liquid-permeable topsheet for the garment allows the crests of the respective ribs to come in contact with the skin of the wearer as the garment is worn because the topsheet is provided with a plurality of inverted V-cross-section ribs extending in parallel one to another in one direction. The upper openings of the respective liquid-passages serving to transfer body fluids to the absorbent core are provided in the planar portions lying at a level lower than the crests of the respective ribs. Consequently, even when the total area of the openings is relatively small with the surface area of the topsheet, this novel topsheet can avoid any apprehension that the topsheet might tightly fit to the skin of the wearer and cause stuffiness and/or eruption.

What is claimed is:

1. A disposable body fluids absorbent garment comprising a liquid-permeable topsheet, a liquid-impermeable backsheet and a liquid-absorbent core disposed therebetween, wherein:

the topsheet has an upper surface adapted to contact a wearer's skin and a lower surface, the upper surface has planar portions extending substantially in a plane and a plurality of ribs extending parallel to one another only in one direction, each rib rising from the lower surface toward the upper surface and having an inverted V-shape in cross-section and a crest defined by an included angle of 10–90°, said crests extending above the planar portion such that adjacent crests define a groove therebetween with associated planar portions forming a bottom of the groove, said grooves thereby also extending only in said one direction, and liquid-passages opening in the planar portions and extending downward through the lower surface from the upper surface, wherein the liquid-passages are arranged intermittently with respect to the direction in which the ribs extend.

2. The garment according to claim 1, wherein the ribs extend transversely of the garment.

3. The garment according to claim 1, wherein the topsheet is made of any one of a nonwoven fabric and a plastic film.

4. The garment of claim 1, wherein said planar portions extend generally in a horizontal plane.

5. The garment of claim 1, wherein inclined surfaces defining said crests are continuous extensions of surfaces defining liquid-passages thereto.

6. A method for making a liquid-permeable topsheet for a disposable body fluids absorbent garment comprising the steps of providing a web having at least one of a nonwoven fabric and a thermoplastic synthetic resin film and feeding said web between at least one pair of first and second rolls arranged in parallel to each other so as to engage each other and thereby to emboss the web, wherein:

the first roll is formed on a smooth surface thereof with a plurality of ribs extending in parallel to an axis of the first roll and each rib has a cross-section in an inverted V-shape and pyramidal recesses are arranged between each pair of the adjacent ribs intermittently in parallel to the axis;

the second roll is formed on a smooth surface thereof with first pyramids adapted to be received by the pyramidal recesses and second pyramids arranged on the same circumferential lines on the second roll alternately with the first pyramids with the respectively adjacent ribs therebetween; and the web is fed between the first and second rolls to form liquid-passages extending in the direction of a thickness of the web toward one direction under the action of the pyramidal recesses and the pyramids, and ribs each presenting a cross-section in an inverted V-shape and projecting toward the other direction are formed at least under the action of the ribs with the first and second pyramids.

7. A disposable body fluids absorbent garment comprising a liquid-permeable topsheet, a liquid-impermeable backsheet and a liquid-absorbent core disposed therebetween, wherein:

said topsheet has an upper surface adapted to contact a wearer's skin and a lower surface, the upper surface has planar portions extending substantially in a horizontal plane, a plurality of ribs extending parallel to one another in one direction, each rib rising from the lower surface toward the upper surface in each of the planar portions and presenting an inverted V-shape in cross-section, and liquid-passages opening in the planar portions and extending downward through the lower surface from the upper surface, wherein the liquid-passages are arranged intermittently with respect to the direction in which the ribs extend, and wherein the ribs extend transversely in the garment.

* * * * *